United States Patent [19]

Hattori et al.

[11] 4,389,569

[45] Jun. 21, 1983

[54] EMISSION COMPUTED TOMOGRAPH

[75] Inventors: Hiroyuki Hattori, Kyoto; Kazuo Uemura, Akita, both of Japan

[73] Assignee: Shimadzu Corporation, Kyoto, Japan

[21] Appl. No.: 214,987

[22] Filed: Dec. 10, 1980

[30] Foreign Application Priority Data

Dec. 14, 1979 [JP] Japan ................................ 54-163317

[51] Int. Cl.³ .............................................. G01T 1/20
[52] U.S. Cl. ................................................ 250/363 S
[58] Field of Search ................. 250/363 S, 360, 445 T, 250/505, 511, 513

[56] References Cited

U.S. PATENT DOCUMENTS

| 3,970,853 | 7/1976 | Kuhl et al. | 250/363 S |
| 4,197,460 | 4/1980 | Anger | 250/363 S |
| 4,289,965 | 9/1981 | Koga et al. | 250/363 S |

Primary Examiner—Alfred E. Smith
Assistant Examiner—Janice A. Howell
Attorney, Agent, or Firm—Fidelman, Wolffe & Waldron

[57] ABSTRACT

An emission computed tomograph provided with a collimator ring rotatable about an object being examined and having a plurality of slits for defining the direction of incidence of the radiation emitted from the object on the radiation detectors. The slits are arranged circumferentially of the ring and directed at successively different angles relative to the radial direction of the collimator ring, so that as the ring is rotated, the object is tomographically scanned. The collimator ring may be divided into a plurality of equal arcuate portions, in each of which the slits are directed toward the object in parallel with each other, so that as the collimator ring is rotated to scan the object, only the parallel profile data thereof can be obtained.

16 Claims, 10 Drawing Figures

EMISSION COMPUTED TOMOGRAPH

Background of the Invention

This invention relates to an emission computed tomograph and a collimator for use therein.

Emission computed tomography commonly referred to as ECT is a technique for obtaining an image of the distribution of radioactivity of radioisotope in a desired plane perpendicular to the axis of the body of a patient within a particular organ thereof by administering to the patient a pharmaceutical compound labelled with the radioisotope, detecting from outside the body the gamma ($\gamma$) radiation emitted by the isotope that has been accumulated in the particular organ and processing the detected data by an electronic computer to obtain the image.

In one known type of emission computed tomograph especially for single photons, the radiation detector is directed to the body of a patient to be examined at different angles within 360° within a plane perpendicular to the axis of the body so that for each of the angles the body is scanned to obtain profile data and the various profile data thus obtained for all the scanning angles are processed by an electronic computer to reconstruct the tomographic image of the body in that plane.

To make scanning with a radiation detector easy, it has been proposed to arrange a plurality of radiation detectors circumferentially about the axis of a human body to be scanned and provide each of the detectors with a collimator connected through a suitable transmission to a common drive, so that all the collimators are simultaneously operated to scan the body in a particular plane perpendicular to the axis of the body.

It has also been proposed to construct such a collimator by a pair of swingable plates of a material capable of blocking radiation provided in front of each of the radiation detectors. A report on the mechanical structure of this type of emission computed tomograph is expected to be published in IEEE Transactions on Plasma Nuclear Sciences in February 1981.

The primary object of this invention is to provide a collimator for use in an emission computed tomograph, which is capable of defining the direction or angle of incidence of radiation on the detector with high accuracy and precision so as to eliminate any artifact in the quality of the tomographic image reconstructed thereby, and which is simple in construction, easy to manufacture and exchange for a different collimator and can be driven by a simple driving mechanism.

Another object of the invention is to provide such a collimator as aforesaid, which makes it possible to obtain data that can be processed by a computer more simply and easily than the data obtained by using the prior art collimators.

Another object of the invention is to provide such a collimator as aforesaid, which makes it possible to obtain only parallel profile data thereby to shorten the time required for processing the data and simplify the process.

Another object of the invention is to provide such a collimator as aforesaid, which is capable of providing selectively high resolution (with low sensitivity) and high sensitivity (with low resolution).

Another object of the invention is to provide an emission computed tomograph provided with such a collimator as aforesaid.

Other objects and advantages of the invention will become apparent from the following description with reference to the accompanying drawings.

SUMMARY OF THE INVENTION

In one embodiment of the invention, the collimator is in the form of an annular body or ring rotatable about an object to be examined and provided with a plurality of slits for defining the direction of incidence of the radiation emitted from the object being examined on the radiation detectors. The slits are arranged circumferentially of the ring and directed at successively different angles relative to the radial direction of the ring, so that as the ring is rotated, the object is tomographically scanned.

In another embodiment of the invention, the collimator is divided into a plurality of equal arcuate portions, in each of which the slits are directed toward the object being examined in parallel with each other, so that as the collimator is rotated to scan the object, only the parallel profile data thereof are obtained.

DESCRIPTION OF PREFERRED EMBODIMENTS

Figure 1:
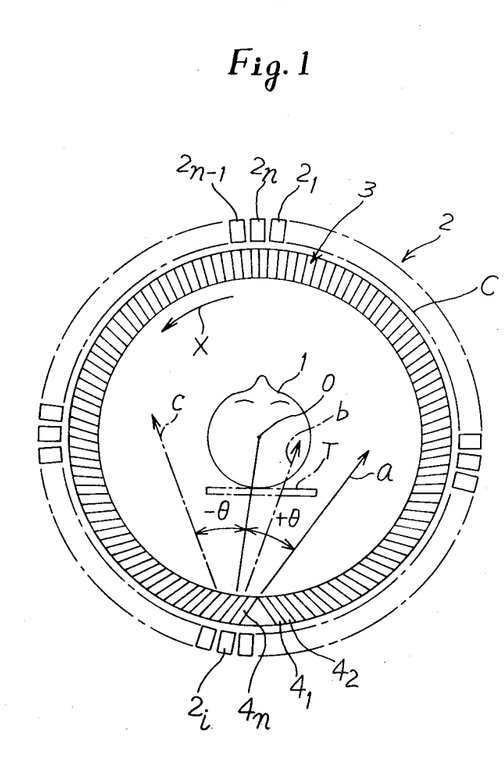
FIG. 1 is a schematic front view of one embodiment of the invention.

Referring now to the drawings, first to FIG. 1, which schematically shows a part of a human body, e.g., the head 1 to be examined supported on a suitable holder or table T. A plurality of radiation detectors $2_1$ to $2_n$ are arranged side by side within a plane perpendicular to the axis of the body and along a circle C whose center coincides with the axis 0 of the body. The circular arrangement of radiation detectors will be referred to collectively as the detector ring 2.

A collimator 3 in the form of a ring is provided concentrically within the circle C or the detector ring 2 and is rotatable about the center 0 in a manner to be described later in detail. The collimator ring 3 comprises a plurality of slits $4_1$ to $4_n$ schematically shown in FIG. 1 arranged circumferentially of the collimator ring 3 so as to regulate the direction of incidence of radiation on each of the detectors $2_1$ to $2_n$. The slits $4_1$ to $4_n$ are directed at successively different angles within the sector-shaped range from $+\theta°$ to $-\theta°$ relative to the radial direction of the collimator ring 3.

Figure 2:
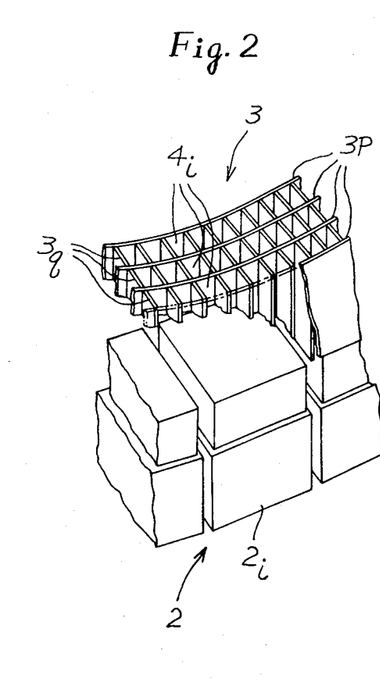
FIG. 2 is a fragmentary perspective view somewhat schematically showing the collimator of FIG. 1.

As fragmentarily shown by way of example in FIG. 2, the collimator 3 comprises a plurality of annular plates $3_p$ of the same dimension coaxially arranged and axially spaced a suitable distance from each other, with a plurality of divider plates $3_q$ disposed between each adjacent two of the annular plates $3_p$ perpendicularly thereto and circumferentially spaced apart from each other so as to divide the space between the adjacent two annular plates into the slits $4_l$ to $4_n$ arranged circumferentially of the collimator ring. In FIG. 2 there are three circumferential arrays of slits axially arranged side by side, each of the circumferential arrays including slits $4_l$ to $4_n$. The arrangement is not essential but preferable since it improves the resolution in the direction of thickness of the slice of the object.

In FIG. 1, suppose that one of the detectors, say, $2_i$ has one of the slits, say, $4_n$ positioned in front of the detecting surface thereof. The direction of incidence of radiation on the detector $2_i$ is as shown by an arrow a, making an angle $+\theta°$ with the radial direction of the collimator ring 3. As the collimator 3 is rotated counterclockwise as shown by an arrow X, the succeeding slits directed at successively decreasing angles relative to the radial direction come to be positioned before the detector $2_i$ so that the angular direction of incidence of radiation on the detector $2_i$ is successively changed from the direction a through b and thence the radial direction toward the center 0 until the direction becomes c when the collimator 3 has been rotated through approximately 360°. This means that the angular direction of incidence of radiation on the detector $2_i$ has been deflected $2\theta°$ from the direction a to the direction c.

The same is true with all the other detectors. Therefore upon one rotation of the collimator ring 3 each of the detectors $2_l$ to $2_n$ has scanned the sector-shaped area of the angle $2\theta$.

Figure 3:
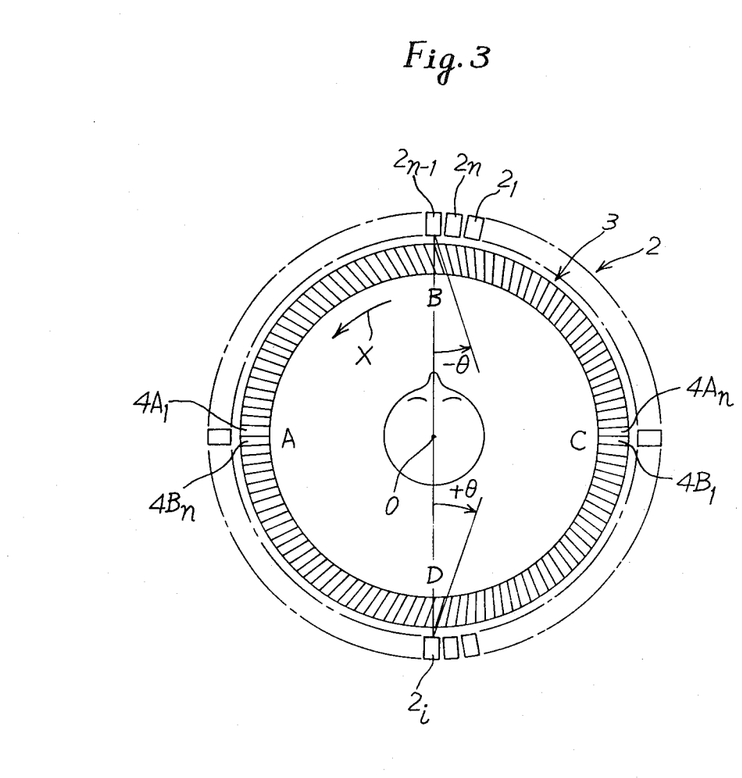
FIG. 3 is a view similar to FIG. 1 but showing another embodiment of the invention.

FIG. 3 shows a collimator ring 3 constructed in accordance with another embodiment of the invention. The collimator is so designed that upon one rotation thereof the direction of incidence of radiation on each of the detectors $2_l$ to $2_n$ changes from one extremity of the sector-shaped area of the angle $2\theta$ between $+\theta°$ and $-\theta°$ to the opposite extremity and back to the one extremity.

To this end the collimator is provided with a first plurality of slits $4A_l$ to $4A_n$ in the semicircle ABC of the collimator ring and a second plurality of slits $4B_l$ to $4B_n$ in the other semicircle CDA thereof. The first group of slits $4A_l$ to $4A_n$ in the semicircle ABC are directed at successively different angles within the range of the angle $\theta$ between 0° and $-\theta°$ relative to the radial direction of the collimator ring 3 so that as the collimator 3 is rotated counterclockwise as shown by the arrow X through 180°, the angular direction of incidence of radiation on the detectors is deflected from 0°, that is, the radial direction toward the center 0 leftward (as the center 0 is viewed radially inwardly from the detectors) as far as $-\theta°$, that is, the direction making an angle $\theta$ to the left with the radial direction and then back to 0° (the radial direction) again.

The second group of slits $4B_l$ to $4B_n$ in the semicircle CDA are directed at successively different angles within the range of the angle $\theta$ between 0° and $\theta°$ relative to the radial direction of the collimator ring 3 so that as the collimator is rotated counterclockwise through 180°, the angular direction of incidence of radiation on the detectors is deflected from 0°, that is, the radial direction toward the center 0 rightward (as the center 0 is viewed radially inwardly from the detectors) as far as $+\theta°$, that is, the direction making an angle $\theta$ to the right with the radial direction and then back to 0° (the radial direction) again.

As can be easily seen, upon one counterclockwise rotation of the collimator each of the detectors scans the sector-shaped area of the angle $2\theta$ between the $+\theta°$ and $-\theta°$ at the opposite sides of the radial direction.

As previously mentioned, the slits of the collimator are directed at successively different angles relative to the radial direction of the collimator ring. If the angular direction of each of the slits is so set as to differ by an equal from the adjacent slits, the following problem will result.

As is well known in the art, in order to reconstruct a tomographic image of an object being examined, profile data in various directions in the tomographic plane are required. In order to obtain such profile data the data in parallel directions only must be collected. However, in the data of any profile the interval or distance between adjacent two sampling positions is greater in the central portion of the scanned area than in the peripheral portion thereof due to the following reasons.

Figure 4:
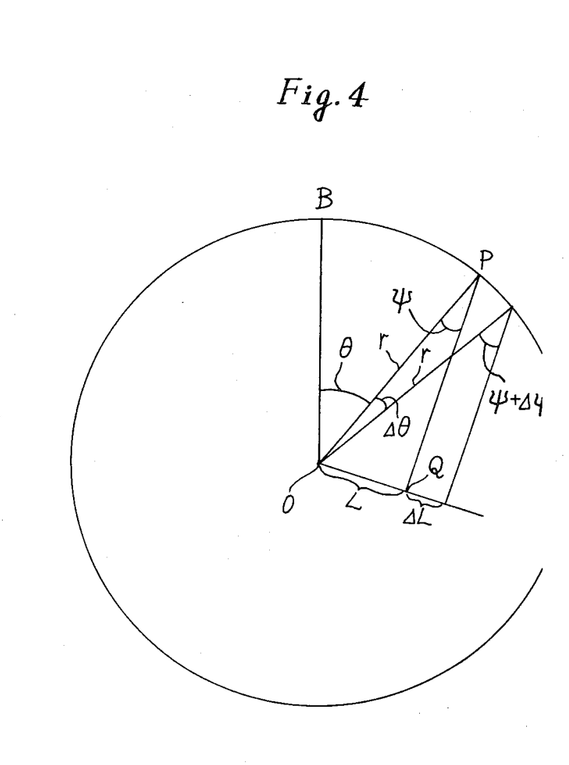
FIG. 4 is a drawing for explaining the manner in which the slits in the collimator are directed in FIG. 1 or 3.

Referring to FIG. 4, let the line OB be the initial line which lies at angle 0° and the position P of each of the slits of the collimator be expressed by the angle $\theta$ that the line OP makes with the initial line OB.

If, as previously mentioned, the angular direction of each of the slits changes by an equal angle from that of the adjacent slit, the direction of the slit or the angle $\Psi$ that the direction or line PQ makes with the radial direction or the line OP can be expressed as:

$$\Psi = f(\theta) = k\theta \qquad (1)$$

wherein k is a constant.

Let the line or radius OB be of a length r and the length L is given as $$L = r \sin \Psi \qquad (2)$$

The space or distance $\Delta L$ between adjacent two data can be expressed as:

$$\Delta L = r \sin(\Psi + \Delta\Psi) - r \sin \Psi \qquad (3)$$

Since the collimator ring is rotated at a constant angular speed and the sampling cycle of the detectors is constant, from the above equations (2) and (3) we obtain $$\frac{dL}{d\theta} = r \cdot \frac{d\Psi}{d\theta} \cdot \cos \Psi \qquad (4)$$

The distance $\Delta L$ is $(dL/d\theta)$ if expressed in the form of differential. When the collimator is made as expressed by equation (1), we obtain $$\frac{dL}{d\theta} = r k \cos \theta \qquad (5)$$

Therefore, as the angle $\theta$ approaches $(\pi/n)$ or $-(\pi/n)$, the distance $(dL/d\theta)$ becomes smaller and smaller, so that the density of the data obtained is not uniform, with the data being relatively sparse in the central portion of the scanned area, where supplementation of data is required to ensure the accuracy of the reconstructed image.

To avoid the above defect and inconvenience, it is better to keep the distance ($dL/d\theta$) constant. In other words, the following relation is very preferable.

$$\frac{dL}{d\theta} = r \cdot \frac{d\Psi}{d\theta} \cdot \cos \Psi = r \cdot f(\theta) \cdot \cos f(\theta) = \text{constant} \quad (6)$$

Solving the above equation, we obtain $$\sin \Psi = K\theta + C \quad (7)$$

wherein K and C are both constants. Since $\Psi = 0$ when $\theta = 0$, $C = 0$, and if the angle $\Psi$ is the maximum ($\Psi = \Psi_{max}$) when $\theta = (\pi/n)$, we obtain $$\Psi = \sin^{-1}\left\{ (\sin \Psi_{max}) \frac{n}{\pi} \theta \right\} \quad (8)$$

where n is an integer which expresses the number of scanning in one rotation of the collimator ring.

Therefore, if the direction or angle $\Psi$ of each of the slits is so determined for the position of the slit (as expressed in terms of $\theta$) as to meet the above equation (8), the parallel data having a uniform data density can be obtained.

Figure 5:
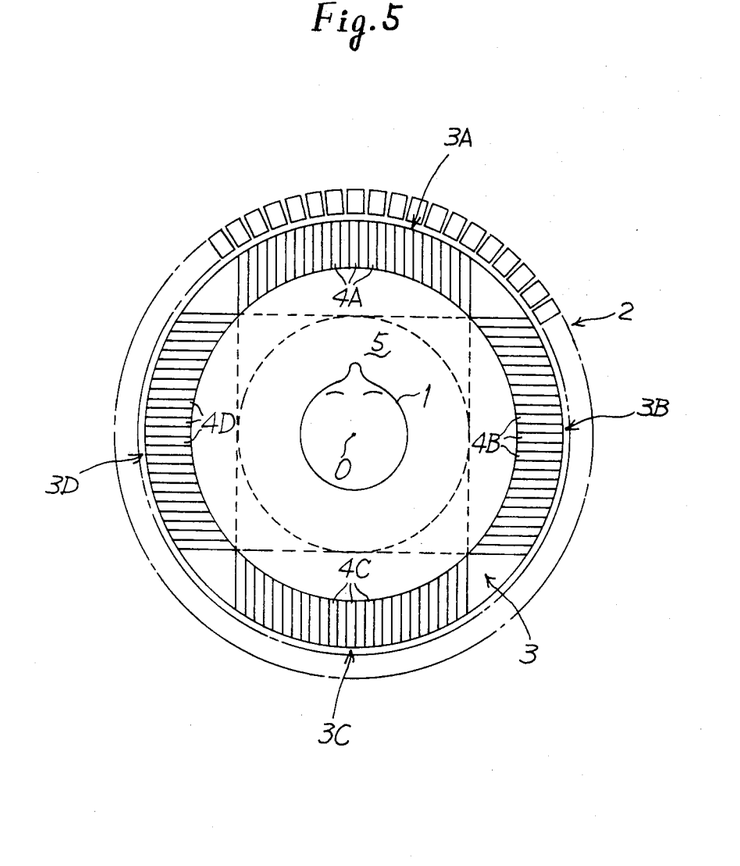
FIG. 5 is a view similar to FIG. 1 but showing a third embodiment of the invention.

FIG. 5 shows a third embodiment of the invention, wherein the collimator 3 is provided with a plurality, say, four groups of slits 4A, 4B, 4C and 4D. The collimator 3 comprises four sections 3A, 3B, 3C and 3D, in each of which one of the four groups of slits are formed in such a manner that they are directed toward the object 1 to be examined and extend in parallel with each other.

The slits may be formed in a manner similar to that in the previous embodiments, with axially spaced annular plates and dividing plates being so arranged as to define the parallel slits between the annular plates. The collimator ring 3 is rotatable about the center 0 as in the previous embodiments.

With the collimator ring 3 being positioned relative to the detector ring 2 as shown in FIG. 5, of all the radiations emitted from the body 1 in all directions only those radiations which advance vertically up and down and horizontally right and left can pass through the slits 4A–4D to enter the detectors behind the slits. Therefore, when the collimator ring 3 has been rotated for a quarter of one rotation, all of the radiations that have been emitted by the body in all directions have entered the detectors so that the necessary data have been obtained. Any radiation emitted in any direction from any point within the area 5 defined by a circular dotted line never falls to enter any of the detectors. In this sense the area 5 may be referred to as the image reconstructing area or the field of view.

In FIG. 5, the collimator is divided into four arcuate sections. It may also comprise as many sections as is desired, for example, two, three, five, six or more sections. With a greater number of sections provided, the number of the detectors which cannot be used (that is, those detectors which are not situated behind the parallel slits and therefore cannot receive radiation) is reduced, but the image reconstructing area 5 becomes smaller.

In any of the previous embodiments, the smaller is the width of the slits in the collimator ring 3, that is, the distance between each adjacent two of the dividing plates $3_q$ in FIG. 2, the higher the resolution becomes, whereas the greater the slit width is, the higher the sensitivity becomes. In accordance with the invention as many collimators of different characteristics as is desired may be provided for selective use in a specific application.

The radiation detectors the number of which is 64 or 72 for example are circumferentially arranged side by side with a gap or a radiation shield between adjacent detectors.

When the collimator of FIG. 1 or 3 is used, the distributions of the data are just like many sectors which have their top at the center of the detectors and completely cover the field of view. Finer data density is required for better reconstructed images. When the detector ring is rotated half the angle between adjacent two of the detectors, the number of the sectors is doubled so that better images can be expected.

An effective way of obtaining a finer data density with the collimator of FIG. 5 is to wobble the entire detector assembly in a short radius, for example approximately 75% of the detector interval in the ring. A concrete arrangement for effecting such rotation or wobbling will be described presently.

Figure 6:
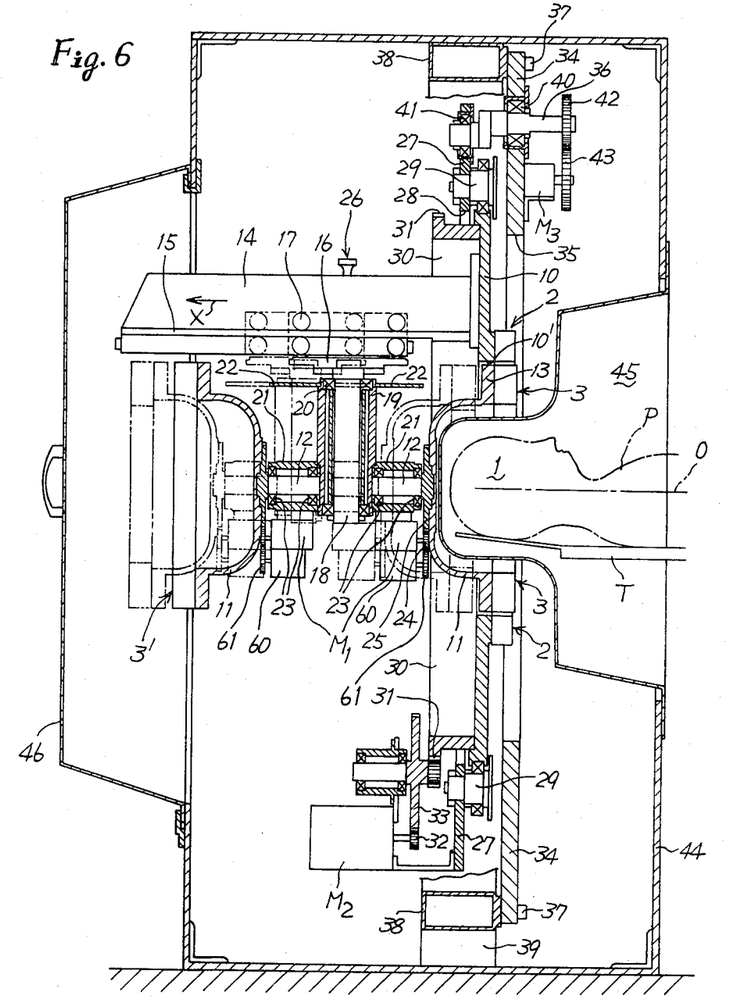
FIG. 6 is a somewhat schematic elevational view, in vertical section, of the emission computed tomograph in one embodiment of the invention.

FIG. 6 shows by way of example a concrete arrangement of an emission computed tomograph constructed in accordance with the invention. There is shown an annular support plate 10 having a central opening 10'. The detector ring 2 comprising a plurality of detectors and schematically shown for simplicity of illustration is fixed to one end face of the inner periphery of the annular plate 10 by means of appropriate mechanical means. Each of the detectors usually comprises a scintillation crystal and a photomultiplier tube though they are shown schematically. The plate 10 is rotatable about a horizontal axis 0 and also capable of wobbling as will be described later in detail.

A bowl 11 is provided with a spindle 12 by which the bowl is rotatable about the horizontal axis 0 and a flange 13 which is disposed concentrically within the central opening 10' of the plate 10. The collimator ring 3 schematically shown for simplicity of illustration is fixed to the flange 13 by adhesive or any appropriate mechanical means, so that the collimator ring 3 is disposed concentrically within the detector ring 2 in radial alignment therewith.

A support arm 14 has its one end fixed to the end face of the annular support plate 10 opposite to the end face to which the detector ring 2 is fixed, and extends horizontally a suitable distance. The arm 14 is provided on the underside thereof with a pair of guide rails only one of which is shown at 15 for guiding a carriage 16 having rollers 17 engaging the rails 15. A vertical rod 18 depends from the carriage 16 and supports a rotatable sleeve 19 through a pair of bearings 20.

Four horizontal support sleeves 21 are fixed to and extend radially from the lower end of the vertical sleeve 19 spaced 90° apart from each other. In FIG. 6 only two of the four horizontal sleeves 21 are shown extending oppositely to the right and left. The spindle 12 of the bowl 11 is rotatably supported by the horizontal sleeve 21 through a pair of bearings 23. The horizontal sleeve also supports a motor $M_1$, which drives a pinion gear 24 meshing with a gear 25 fixed to the bowl 11.

The other three horizontal sleeves, only one of which is shown oppositely to the one described just above, have a bowl 11 of the same construction as the one above-mentioned but with a collimator of different characteristics as shown at 3'. In other words, there are four bowls 11 provided about the vertical sleeve 19 spaced 90° apart from each other so that four different types of collimators are available for selective use in the manner to be described presently. Two of the collimators may be designed for positron annihilation gamma rays.

To exchange the collimator 3 shown in the operative position in FIG. 6 for the other collimator 3', a locking means 26 is released and the carriage 16 together with the various parts and members carried thereby is moved leftward as shown by an arrow X as far as the collimator ring 3 is out of radial alignment with the detector ring 2 as shown by the dash-and-dot line. Then, the vertical sleeve 19 is rotated to bring one of the three bowls 11 which has the desired type of collimator to the position where the previous bowl has been. A disc 22 fixed to the upper end of the vertical sleeve 19 cooperates with an appropriate member not shown but carried by the carriage 16 to maintain the vertical sleeve 19 in the rotated position. Then the carriage 16 with everything thereon is moved rightward to bring the selected collimator ring into radial alignment with the detector ring with the locking means 26 operated to fix the carriage in position. Thus the apparatus can be operated selectively with a high resolution collimator, a high sensitivity collimator, or a collimator for position annihilation gamma rays.

An annular plate 27 capable of wobbling motion has a central opening 28 in which the support plate 10 with everything carried thereby is positioned. The wobble plate 27 is also provided with a plurality, say, four rollers 29 circumferentially spaced 90° apart from each other and engaging the peripheral edge of the support plate 10 so as to support the plate 10 rotatably about the axis 0.

A ring gear 30 having external teeth 31 is fixed to the end face of the annular support plate 10 opposite to the end face to which the collimator ring 2 is fixed. A motor $M_2$ is mounted on the wobble plate 27 and rotates a pinion 32 which in turn rotates the ring gear 30 and consequently the detector ring 2 through a reduction gear 33 for the purpose to be described later.

A stationary annular plate 34 having a central opening 35 is provided with a plurality, say, three crank shafts 36 spaced 120° apart from each other, only one of which is shown in FIG. 6 for simplicity of illustration. The stationary annular plate 34 is held upright, that is, with its plane extending vertically and fixed by means of bolts 37 to an annular frame 38 which is in turn fixed to a base member 39. The detector ring 2 and everything inside the ring are positioned inside the opening 35 of the stationary annular plate 34.

Each of the crank shaft 36 is rotatably supported by the stationary annular plate 34 through a bearing 40 and supports the wobble plate 27 through a bearing 41. A gear 42 is fixed to each of the crank shaft 36 and meshes with a drive gear 43 rotated by a motor $M_3$ mounted on the stationary support plate 34.

Figure 7:
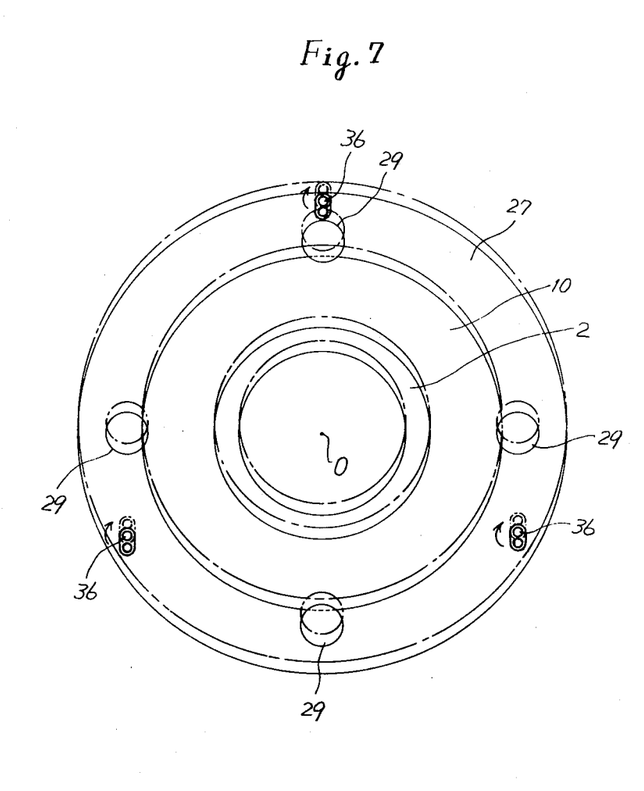
FIG. 7 is a schematic view for explaining the wobbling motion of the detector and collimator rings in FIG. 6.

As the motor $M_3$ is rotated, the crank shafts 36 cause the support plate 27 with everything carried thereon to wobble about the axis 0 as shown in FIG. 7.

A gantry 44 encloses all of the above-mentioned parts and members and is provided at one end face thereof with a recess 45 inwardly projecting through the collimator ring 3 into the bowl 11. In the recess 45 one end of the table T is positioned removably therefrom. The gantry 44 is also provided at the opposite end face thereof with a door 46 for access to the interior mechanism for operation, adjustment, repair or any other necessary work.

Figure 8:
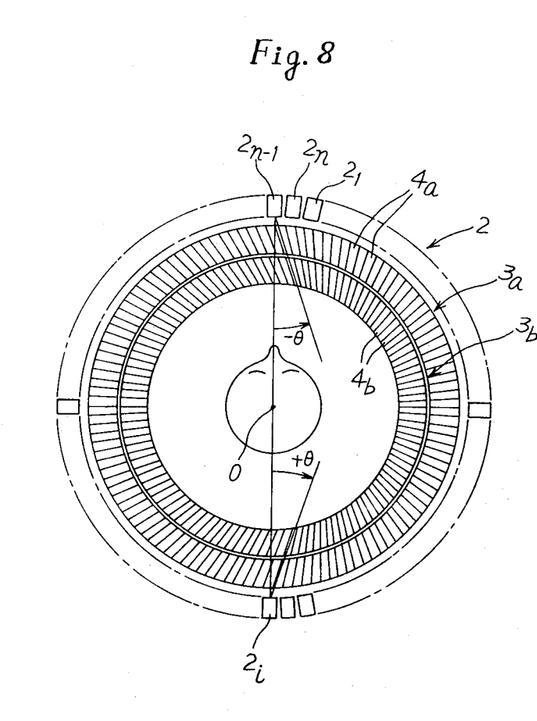
FIG. 8 is a view similar to FIG. 1 but showing a multiconcentric ring collimator.
Figure 9:
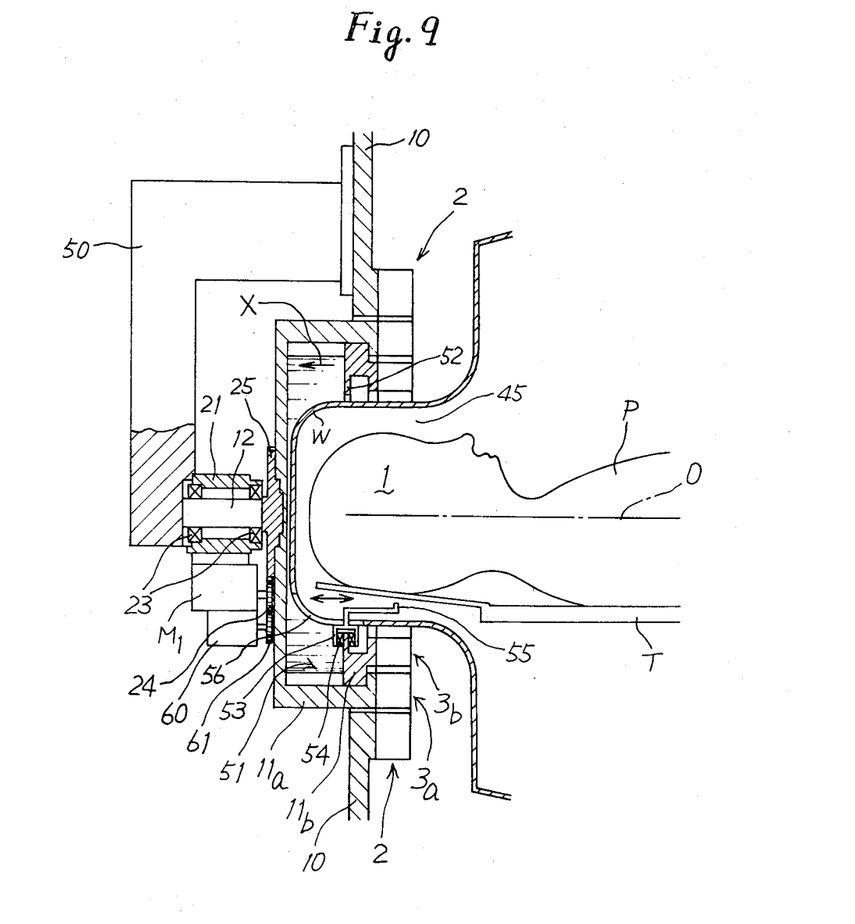
FIG. 9 is a view similar to FIG. 6 but with the collimator of FIG. 8.

FIGS. 8 and 9 show another arrangement that enables selective use of a higher resolution (but with a lower sensitivity) or a lower resolution (but with a higher sensitivity).

The collimator provided inside the detector ring 2 comprises an outer collimator ring 3a and an inner collimator ring 3b (both schematically shown for simplicity of illustration) concentric with the outer ring. The two component rings 3a and 3b are provided with slits 4a and 4b formed and arranged in a manner similar to that in the previous embodiment of FIG. 1 or 3. The slits 4a and 4b are related to each other in a manner to be described in detail presently.

The outer collimator ring 3a is fixed axially to an outer hollow cylindrical support member 11a provided with a spindle 12 by which the member 11a is rotatable about the axis 0 and a gear 25 meshing with a pinion gear 24 driven by a motor $M_1$. The spindle 12 is rotatably supported by a sleeve 21 through a pair of bearings 23. The sleeve is fixed to the lower end of an L-shaped arm 50 fixed to an annular support plate 10. Those component parts which are not shown in FIG. 9 are substantially the same as in FIG. 6 except that in FIG. 9 there is no such means for exchanging the bowls 11 as shown in FIG. 6.

The inner collimator ring 3b is also fixed axially to an inner support ring 11b. The inner collimator ring 3b and the inner support member 11b are concentrically disposed within the outer collimator ring 3a and the outer support member 11a in such a manner that the outer and inner support members (and consequently the outer and inner colimator rings) are rotated simultaneously at the same angular speed, but that the inner support member 11b with the inner collimator ring 3b can be axially slid relative to the outer support member 11a as shown by an arrow X by means of, say, a spline connection 51 thereby to displace the inner collimator ring 3b out of radial alignment with the outer collimator ring 3a.

The inner support ring 11b is provided with an inner circumferential rib 52. A slide 53 engages the rib 52 through a bearing 54 so that as the support member 11a and 11b are rotated, the slide 53 slides circumferentially along the rib 52. A handle lever 55 is fixed to the slide 53 and extends through an axial slot 56 formed in the wall W of the recess 45 of the gantry 44. With the end portion of the table T removed from inside the recess 45, by moving the handle lever 55 axially in either direction as shown by a double-headed arrow it is possible to move the inner collimator ring 3b selectively out of or into radial alignment with the outer collimator ring 3a.

With the two collimator rings radially aligned as shown in FIG. 9, each corresponding two of the slits 4a and 4b in the outer and inner collimator rings 3a and 3b are directed in the same direction and linearly aligned so that as the two collimator rings are rotated as a single whole, the radiation emitted from the object being examined may pass through the aligned slits in the two rings to enter the detector therebehind.

When the slits 4a and 4b in the outer and inner collimator rings 3a and 3b are radially aligned in the above manner, the length of the slit for defining the direction of incidence of radiation on each of the detectors becomes longer than otherwise so that the direction of incidence of radiation can be defined with a higher accuracy and consequently a higher resolution can be obtained.

When the inner collimator ring 3b is disposed axially out of radial alignment with the outer collimator ring 3a, the latter ring alone remains to define the direction of incidence of radiation, so that the accuracy with which the direction of incidence of radiation on the detector is defined is reduced and the resolution is lowered. However, the amount of the radiation incident on the detectors increases with resulting increase in the sensitivity.

In the illustrated embodiment, the collimator comprises a pair of concentric rings. The collimator may also comprise three or more adjacent concentric rings, the inner ones of which are between the outermost and innermost rings and are so arranged as to be axially displaceable from the outermost ring successively from the innermost ring first. This arrangement enables more delicate adjustment of the resolution and sensitivity of the apparatus.

In operation, as the collimator ring is rotated with a position detector 60 detecting the angular position of the collimator ring, the head 1 of a patient P being examined is tomographically scanned with the radiation emerging from inside the head passing through the slits to enter the radiation detectors. The position detector 60 may be connected to the motor $M_1$ by means of, e.g., a gear 61 meshing with the gear 24 so that the rotational angle of the collimator can be detected by decoding the output of the position detector 60.

Figure 10:
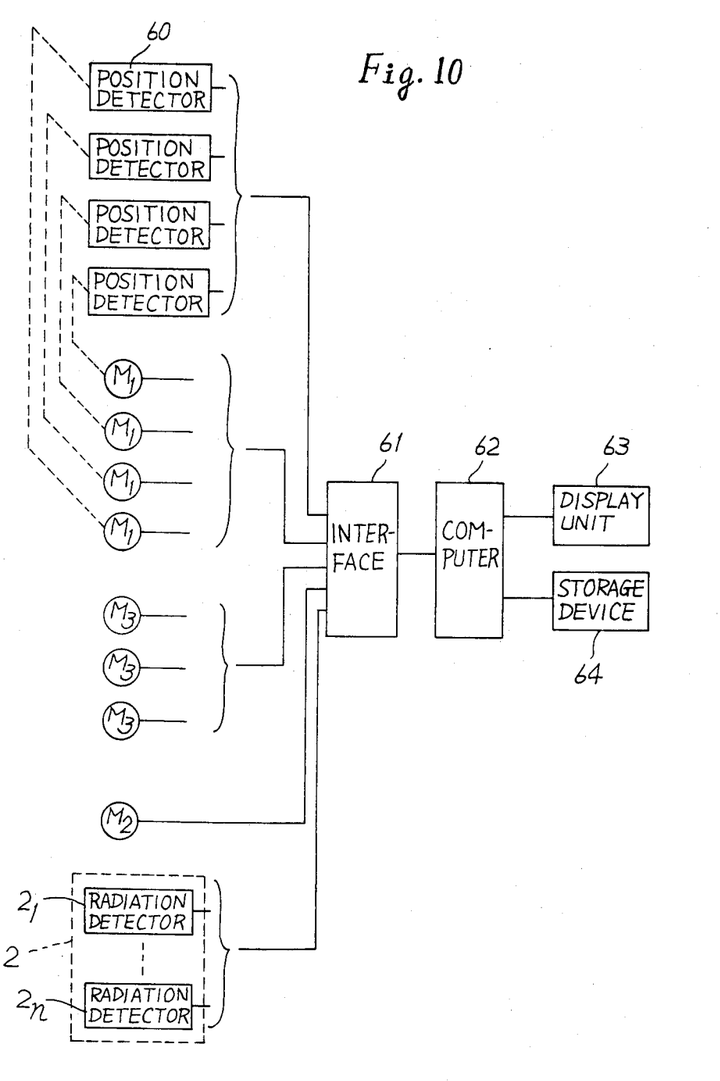
FIG. 10 is a block diagram of the control circuit.

Referring to FIG. 10, the data collected from the radiation detectors as well as from the position detector 60 are transmitted through an interface 61 to an electronic computer 62 where they are processed so as to reconstruct a tomographic image of the object, which is displayed on a suitable display unit 63 and/or recorded in a data storage device 64.

The motors $M_1$ to $M_3$ may be controlled by the computer 62 in accordance with a predetermined program.

Since the collimator of the invention has no movable parts but is formed as a mechanically integral whole, the direction of incidence of radiation onto the detectors can be defined with a higher accuracy and precision than in the prior art machines in which the collimators are separately operated.

The construction and the driving mechanism of the apparatus of the invention is simple and easy to manufacture, and has various other advantages obvious to those skilled in the art.

What we claim is:

1. An emission computed tomograph comprising: means for supporting an object to be examined at a predetermined position so that the axis of said object coincides with a center, said object having taken therein a radionuclide that emits penetrating radiation such as gamma radiation; a plurality of radiation detectors; means for supporting said detectors side by side along a circle about said center so that the radiation incident planes of said detectors face said object so as to receive radiation from said object; collimating means disposed between said predetermined position and said detectors concentrically with said circle and provided with a plurality of slits arranged side by side circumferentially about said center for regulating said radiation emitted from said object so as to enter said detectors; means for supporting said collimating means rotatably about said center; and means for causing said collimating means to be rotated about said center so that those of the radiations emitted from said object which have a direction defined by each of said slits successively enter the corresponding one of said detectors thereby to tomographically scan said object.

2. The apparatus of claim 1, wherein said collimating means comprises a single collimator ring provided with a plurality of slits defined by dividing members of a material impervious to said radiation and arranged side by side circumferentially of said ring.

3. The apparatus of claim 1, wherein said collimating means comprises a plurality of adjacent, separate and concentrically disposed collimator rings, including an inner ring and an outer ring, each of said collimator rings being provided with a plurality of slits defined by dividing members of a material impervious to said radiation, the slits in the collimator rings being disposed so that a slit in one ring is radially aligned with a corresponding slit in an adjacent collimator ring; said collimator rings being rotatable about said center as a single whole, with the inner and any adjacent collimator ring between the inner and outer rings collimator rings being successively and axially slidable, commencing with the inner ring, so as to move the slits of the inner collimator ring or the slits of an adjacent collimator ring, as may be applicable, out of radial alignment with the corresponding slits of the outer collimator ring.

4. The apparatus of claim 1, wherein said collimating means comprises a plurality of separate collimator rings of different characteristics, and further including means for positioning said collimator rings selectively in front of said detectors.

5. The apparatus of claim 1, wherein said slits are arranged over substantially 360° about said center and directed at successively different angles relative to the radial direction of said circle.

6. The apparatus of claim 1, wherein said slits are divided into a plurality of groups, the slits of each of said groups being arranged in one of the equally divided arcuate portions of a circle about said center and directed at successively different angles relative to the radial direction of said circle.

7. The apparatus of claim 1, wherein said slits are divided into a plurality of groups, the slits of each of said groups being arranged in one of the equally divided arcuate portions of a circle about said center and directed toward said object in parallel with each other.

8. The apparatus of claim 1, wherein said slits are directed in such a manner that the angle $\Psi$ that the direction of each of said slits makes with the radial direction of said circle is equal to $$\sin^{-1}\{(\sin \Psi_{max})(n/\pi)\theta\}$$

wherein $\theta$ is the angular position of said each slit on the circumference of said circle, $\Psi_{max}$ is the value of the angle $\Psi$ when $\theta = (\pi/n)$, and n is an integer which expresses the member scanning in one rotation of the collimator ring.

9. The apparatus of claim 1, further including means for causing said first and second supporting means together to rotate about said center.

10. The apparatus of claim 1, further including means for angularly displacing said detectors relative to said collimating means so that those radiations that would otherwise be incident on the areas between adjacent ones of said detectors could be incident on said detectors.

11. A collimator for use in an emission computed tomograph comprising an annular body rotatable about its axis and a plurality of slits formed in said body and arranged side by side circumferentially thereof for regulating the direction of incidence of radiation on the radiation detectors of said tomograph.

12. The collimator of claim 11, wherein said slits are directed at successively different angles relative to the radial direction of said annular body.

13. The collimator of claim 11, wherein said annular body comprises a plurality of arcuate portions and said slits are divided into a plurality of groups so that the slits of each of said groups are provided in one of said arcuate portions of said annular body.

14. The collimator of claim 13, wherein said slits of each of said groups are directed at successively different angles relative to the radial direction of said annular body.

15. The collimator of claim 13, wherein said slits of each of said groups are directed in parallel with the radial direction of said annular body perpendicular to the chord subtended by said one arcuate portion of said annular body.

16. The collimator of claim 11, wherein said slits are directed in such a manner that the angle $\Psi$ the direction of each of the slits makes with the radial direction of said annular body is equal to $$\sin^{-1}\{(\sin \Psi_{max}(n/\pi)\theta\}$$

wherein $\theta$ is the angular position of said each slit on said circle, $\Psi_{max}$ is the value of the angle $\Psi$ when $\theta = (\pi/n)$, and n is an integer which expresses the member scanning in one rotation of the collimator ring.

* * * * *